(12) United States Patent
Nakajima et al.

(10) Patent No.: US 10,039,541 B2
(45) Date of Patent: Aug. 7, 2018

(54) RETRACTOR

(71) Applicants: TOKUSEN KOGYO CO., LTD., Hyogo (JP); OSAKA UNIVERSITY, Osaka (JP)

(72) Inventors: Kiyokazu Nakajima, Osaka (JP); Hiroyuki Yamashita, Hyogo (JP)

(73) Assignees: TOKUSEN KOGYO CO., LTD., Hyogo (JP); OSAKA UNIVERSITY, Osaka (JP)

( * ) Notice: Subject to any disclaimer, the term of this patent is extended or adjusted under 35 U.S.C. 154(b) by 252 days.

(21) Appl. No.: 15/111,846

(22) PCT Filed: Jan. 16, 2015

(86) PCT No.: PCT/JP2015/051039
§ 371 (c)(1),
(2) Date: Jul. 15, 2016

(87) PCT Pub. No.: WO2015/108137
PCT Pub. Date: Jul. 23, 2015

(65) Prior Publication Data
US 2016/0331364 A1    Nov. 17, 2016

(30) Foreign Application Priority Data
Jan. 16, 2014    (JP) .................. 2014-005685

(51) Int. Cl.
*A61B 17/02* (2006.01)
*A61B 17/34* (2006.01)
(Continued)

(52) U.S. Cl.
CPC ...... *A61B 17/0218* (2013.01); *A61B 17/3478* (2013.01); *A61B 1/00087* (2013.01); *A61B 2017/00853* (2013.01)

(58) Field of Classification Search
CPC .................. A61B 17/0218; A61B 2017/00349
See application file for complete search history.

(56) References Cited

U.S. PATENT DOCUMENTS 5,454,365 A    10/1995    Bonutti
5,678,572 A    10/1997    Shaw et al.
(Continued)

FOREIGN PATENT DOCUMENTS

CN    1925806 A    3/2007
EP    2260772 A1    12/2010
(Continued)

OTHER PUBLICATIONS

Office Action in CN Application No. 201580004786.7 dated Nov. 6, 2017, 15 pages.
(Continued)

*Primary Examiner* — Andrew Yang
(74) *Attorney, Agent, or Firm* — Marshall, Gerstein & Borun LLP

(57) ABSTRACT

The present invention is a retractor for displacing an organ within the body cavity or the inner wall of a hollow organ, the retractor being provided with: a housing tube; an expansion body which can be housed into and extend from the housing tube; and a grip connected to the proximal ends of the housing tube and the expansion body. The expansion body is provided with: a displacing part configured from a movable wire and multiple fixed wires disposed in the periphery of the moveable wire; and an introduction tube which is disposed along the displacing part and through which the movable wire penetrates. Moreover, when the expansion body is expanded, the displacement part is designed so that, from among the expansion angles formed by two adjacent fixed wires, one expansion angle ($\theta 2$) becomes larger than the other expansion angle ($\theta 1$).

7 Claims, 9 Drawing Sheets

(51) Int. Cl.
    *A61B 1/00*         (2006.01)
    *A61B 17/00*        (2006.01)

(56) References Cited

U.S. PATENT DOCUMENTS

| | | |
|---|---|---|
| 2005/0182417 A1 | 8/2005 | Pagano |
| 2006/0116690 A1 | 6/2006 | Pagano |
| 2010/0076445 A1 | 3/2010 | Pagano |
| 2013/0324795 A1 | 12/2013 | Nakajima et al. |

FOREIGN PATENT DOCUMENTS

| | | |
|---|---|---|
| EP | 2679169 A1 | 1/2014 |
| JP | 06-154152 A | 6/1994 |
| JP | 8-317928 | 12/1996 |
| JP | 2005-349000 A | 12/2005 |
| WO | WO-2012/114569 A1 | 8/2012 |

OTHER PUBLICATIONS

Extended European Search Report in EP Application No. 15737127.9 dated Sep. 13, 2017, 7 pages.
Search Report in International Application No. PCT/JP2015/051039 dated Mar. 17, 2015, 4 pages.
English Translation—International Preliminary Report on Patentability and Written Opinion for International Application No. PCT/JP2015/051039 dated Jul. 19, 2016.

RETRACTOR

CROSS-REFERENCE TO RELATED APPLICATIONS

This application is based upon and claims the benefit of priority of the prior Japanese Patent Application No. 2014-005685, filed on Jan. 16, 2014, the entire contents of which are incorporated herein by reference.

TECHNICAL FIELD

The present invention relates to retractors, and more specifically, to a retractor that can be developed in a three-dimensional direction to be used to exclude an inside wall of a hollow organ or an organ in a body cavity.

BACKGROUND ART

In a conventional laparotomy, the organ that inhibits the surgery can be manually spread, but it is known that the organ cannot be easily spread and that it is difficult to ensure a field of view optimum for the surgery under endoscopic surgery. For example, a method of injecting gas into the body cavity to ensure the field of view and the operation space is known, but such method requires full anesthesia and the invasiveness is not actually low.

To alleviate the problem of field of view, and the like and to facilitate the endoscopic treatment, an instrument called a retractor that excludes or tugs an organ to be treated or an organ that inhibits the field of view during the treatment, and the like, has been developed. As a basic function, it is desired that an instrument can be inserted through a small opening passage such as a trocar (pallium tube) or a small incision that serves as an insertion passage when inserting the retractor into the body. Therefore, the retractor needs to have a small diameter (e.g., desirably smaller than or equal to 10 mm in the case of trocar, and smaller than or equal to 20 mm in the case of small incision) and to have a rod-like form at least at the time of insertion, whereas after the insertion into the body cavity, the retractor is demanded to be deformable to a shape an excluding section has a large area of a certain degree to widely and safely exclude the target.

According to the conflicting demands described above, variously devised retractors are being proposed and are commercially available. For example, the retractor in which the excluding section opens to a fan shape has been provided (e.g., Patent Literature 1). At the time of insertion of the trocar into the abdominal cavity, a fan-shaped excluding section is folded and accommodated inside a rod-shaped tube, and is pushed out by the rod-shaped tube in the body cavity to be spread to a fan shape. A structure of opening the fan-shaped excluding section to an arbitrary size by manual operation and a structure in which an angle between the excluding section and a base section varies are known, where such structures are suited for excluding liver and intestine as the advantage thereof is that the organ can be excluded relatively widely. The shape is not limited to a fan shape, and various shapes such as a diamond shape, and the like have also been proposed.

In particular, development of a retractor that more effectively excludes the organ and that excels in operability is desired.

Furthermore, among such operability, when various types of surgeries using the retractor are carried out, the developed retractor and another surgical device (e.g., electronic surgical knife) may be brought into contact carelessly thus generating sparks in the operative field. Thus, a more careful task to prevent such contact is required on the operator. Such task is a load that forces extreme strain over a long time to the operator, and the surgery of a long time may amplify physical load for the patient as well.

CITATION LIST

Patent Literature

Patent Literature 1: JP 6-154152 A

SUMMARY OF INVENTION

Technical Problem

The present invention aims to solve the problems described above, and the object thereof is to provide a retractor that widely ensures an operative field, reduces the generation of sparks in the operative field caused by careless contact of the developed retractor and another surgical device (e.g., electronic surgical knife), and alleviates the psychological and physical load of the operator and the patient.

Solution to Problem

The present invention is a retractor for excluding an inside wall of a hollow organ or an organ in a body cavity, and the retractor includes:
 an accommodation tube;
 a developing body that is configured to be accommodated and extended with respect to the accommodation tube; and
 a grip connected to respective proximal ends of the accommodation tube and the developing body, wherein
 the developing body includes
 an excluding section configured by a movable wire and at least three fixing wires arranged at a periphery of the movable wire, and
 an introducing tube extended from the excluding section, the movable wire being passed through the introducing tube;
 a distal end of the movable wire and a distal end of the fixing wire are joined in the excluding section;
 among developing angles formed between two adjacent fixing wires in the excluding section when the developing body is developed, one developing angle $\theta 2$ is greater than a remaining developing angle $\theta 1$; and
 the developing angle $\theta 2$ is 90° to 240°.

In one embodiment, the accommodation tube is a rigid perforation tube.

In further embodiment, the excluding section is flexed with respect to an axial direction of the perforation tube when the developing body is developed.

In one embodiment, the grip includes a first grip portion, a second grip portion, and a third grip portion from a distal side;
 a proximal end of the accommodation tube is connected to the first grip portion;
 a proximal end of the introducing tube of the excluding section is connected to the second grip portion; and
 a proximal end of the movable wire of the excluding section is connected to the third grip portion.

In one embodiment, a cross-section of the movable wire has a substantially circular shape.

In one embodiment, a curve of the fixing wire in the excluding section is controlled by pushing or pulling at least one of the second grip portion or the third grip portion with respect to the first grip portion.

In one embodiment, the accommodation tube is a longitudinal tube having flexibility.

Advantageous Effects of Invention

According to the present invention, a retractor that can freely exclude the organ can be provided. The retractor of the present invention has a developing angle θ2, formed between one fixing wire and another adjacent fixing wire of the excluding section, of greater than another developing angle θ1 when the developing body is developed, and thus the developing space configured by the developing angle θ2 becomes wider than the developing space configured by the developing angle θ1, and a wide operative field with enhanced operability of the operator can be obtained. As a result, when also using with a surgical device including an energy element such as an electronic surgical knife, the probability of undesired sparks being generated by the mistaken contact of the device and the fixing wire can be significantly reduced.

BRIEF DESCRIPTION OF DRAWINGS

FIG. 2A is a schematic view of the retractor showing a state in which the developing body is accommodated in a rigid perforation tube, FIG. 2B is a schematic view of the retractor showing a state in which the developing body is extended from the perforation tube to carry out a cocoon-shaped development in an excluding section of the developing body, and FIG. 2C is a schematic view of the retractor showing a state in which a cocoon-shaped structure is developed in the excluding section of the developing body extended from the perforation tube.

FIG. 3A is a cross-sectional view in a longitudinal direction of a distal end portion of the retractor of the present invention showing a state in which the developing body is accommodated in the perforation tube, and FIG. 3B is a partially cutout cross-sectional view of the distal end portion of the retractor of the present invention showing the developing body extended from the perforation tube and in which the cocoon shape is developed.

FIG. 4A is a cross-sectional view of the undeveloped excluding section in which a movable wire has a substantially circular cross-section and a fixing wire having a substantially similar cross-sectional shape is arranged at a part of the periphery of the movable wire, FIG. 4B is a cross-sectional view of the undeveloped excluding section in which the movable wire has a cross-section of a shape combining an arc and a chord, FIG. 4C is a cross-sectional view of the undeveloped excluding section in which the movable wire has a cross-section of a shape where a projection is provided at one part of the chord in the shape combining the arc and the chord, and FIG. 4D is a cross-sectional view of the undeveloped excluding section in which the movable wire has a substantially circular cross-section, and the fixing wire having a substantially similar cross-sectional shape is arranged at a part of the periphery of the movable wire, the number of fixing wires being arranged at the periphery of the movable wire being greater than in FIG. 4A.

FIG. 7A is a view showing one example of the tip of the distal end when configured by five fixing wires and when the developing angle θ1 is approximately 45° and the developing angle θ2 is approximately 180°, and FIG. 7B is a view showing one example of the tip of the distal end when configured by six fixing wires and when the developing angle θ1 is approximately 45° and the developing angle θ2 is approximately 135°.

FIG. 8A is a view showing a state in which the first grip portion, and the second grip portion and the third grip portion are separated when the developing body is accommodated in the perforation tube, FIG. 8B is a view showing a state in which the developing body is extended from the perforation tube, and the first grip portion and the second grip portion, and the second grip portion and the third grip portion are respectively brought into contact, and FIG. 8C is a view showing a state in which the developing body is extended from the perforation tube, and the first grip portion, and the second grip portion and the third grip portion are separated.

DESCRIPTION OF EMBODIMENTS

The present invention will be described in detail using the drawings.

Figure 1:
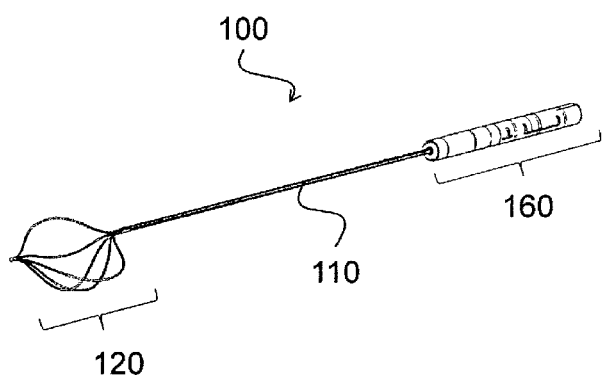
FIG. 1 is a view schematically showing one example of a retractor of the present invention, and is a perspective view of the retractor showing a state in which a developing body is developed.

FIG. 1 is a view schematically showing one example of a retractor of the present invention, and is a perspective view of the retractor showing a state in which a developing body is developed.

A retractor 100 of the present invention includes a developing body 120, a rigid or hard perforation tube 110 serving as an example of an accommodation tube capable of accommodating and including in an extending manner the developing body 120, and a grip 160 connected to respective proximal ends of the perforation tube 110 and the developing body 120.

Figures 2A, 2B, 2C:
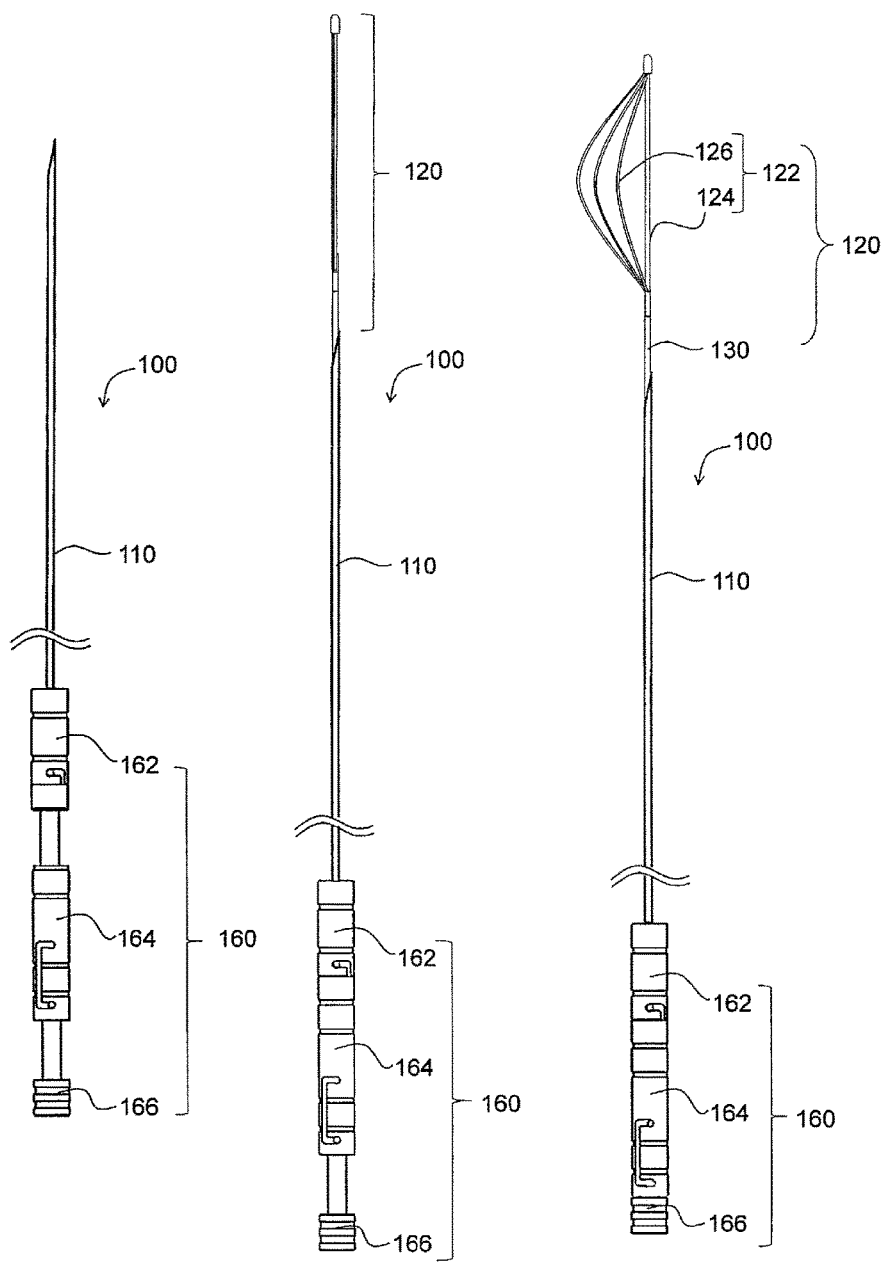
FIGS. 2A to 2C are views showing the retractor of the present invention shown in FIG. 1, where

FIGS. 2A to 2C are side views of the retractor 100 of the present invention shown in FIG. 1. As shown in FIG. 2A, the retractor 100 of the present invention has, for example, the developing body completely accommodated in the perforation tube 110 immediately before use. The proximal end of the perforation tube 110 is connected to a first grip portion 162 of the grip 160.

The term "retractor" used in the present specification refers to a medical instrument for excluding, spreading, tugging, or elevating a target (e.g., organ) or anything that inhibits a field of view in a medical field, and for example, includes a trocar and a pallium tube. The operations of excluding, spreading, tugging, or elevating are sometimes collectively referred to as "retraction" or "retract". When simply referring to "exclusion" in the present specification, this may include not only the operation of exclusion but also operations of spreading, tugging, or elevating (i.e., refers to retraction). The retractor includes an excluding section, as will be hereinafter described, for example, and is required to have such excluding section deformable to a size of a certain extent after being inserted into the body.

The term "distal" used in the present specification refers to a position far from the person operating the retractor, and the term "proximal" refers to a position close to the person operating the retractor as opposed to the term "distal". Thus, the term "distal end" represents an end farthest (i.e., at distant) from the operating person, and the term "proximal end" represents an end closest (i.e., at proximate) to the operating person when operating the retractor of the present invention.

When referring again to FIG. 2A, in one embodiment, the perforation tube 110 is, for example, configured from a straight tube cut such that the distal end side has a sharp pointed shape. The angle of a tip of the distal end of the perforation tube 110 is not particularly limited, but is processed to an angle (e.g., 20° to 50°) at which the perforation into the body is facilitated. The outer diameter of the perforation tube 110 is preferably 1.7 mm to 3.5 mm, and more preferably 2.2 mm to 3 mm. Furthermore, the inner diameter of the perforation tube 110 can be selected from a range of preferably 1.5 mm to 3 mm, and more preferably 1.6 mm to 2.2 mm with respect to the outer diameter. In the present invention, the shape of the tip of the distal end of the perforation tube 110 is not necessarily limited to the description made above, and for example, may have an arbitrary shape that can be adopted to the pallium tube or the trocar in the medical field.

Such perforation tube 110 is preferably made from a rigid material, for example, metal such as stainless steel, tantalum, cobalt alloy, nitinol (nickel-titanium alloy), and the like. The stainless steel includes, for example, SUS304, SUS316, and SUS316L. The retractor 100 of the present invention can reliably perforate a desired position (e.g., abdominal cavity) without being concerned about deflection, bend, breakage, and the like of the perforation tube by using the perforation tube 110 made from such rigid material for the accommodation tube. Furthermore, as the perforation tube 110 is rigid, sufficient strength can be maintained even in the cocoon-shaped development in the excluding section, to be described later, and the retraction.

The grip 160 is divided into three portions, a first grip portion 162, a second grip portion 164, and a third grip portion 166 in the order from the distal end side. The type of material configuring the grip 160 is not particularly limited. The grip 160 is made, for example, from resin such as ABS resin, polycarbonate resin, acryl resin, and the like, metal such as stainless steel, aluminum, and the like, and the combination thereof.

FIG. 2B is a view schematically showing one example of the retractor 100 of the present invention, and is a schematic view of the retractor 100 showing a state in which the developing body 120 is extended from the perforation tube 110 to carry out a partial cocoon-shaped development in the excluding section of the developing body.

In the present specification, the term "cocoon shape" is a shape formed by the curve of a plurality of fixing wires, to be described later, in the excluding section of the developing body, and for example, includes a shape of a cocoon-like or oval sphere (rugby ball, etc.), and is sometimes referred to as "complete cocoon shape" to distinguish from "partial cocoon shape", to be described later. Moreover, in the present specification, the term "partial cocoon shape" refers to that in which a part of the cocoon shape is cut along a direction parallel to the long axis of the complete cocoon shape.

The retractor 100 of the present invention can take in and out the developing body 120 accommodated in the perforation tube 110 by pushing and pulling at least one of the second grip portion 164 and the third grip portion 166 in the grip 160 with respect to the first grip portion 162. The developing body 120 is designed to a size having an outer diameter of preferably 1.5 mm to 3 mm, and more preferably 1.6 mm to 2 mm, and so as to freely slide in the perforation tube 110 when accommodated in the perforation tube 110 (state in which development described later is not carried out). The entire length of the retractor of the present invention is not necessarily limited and, for example, a distance from the distal end to the proximal end of the perforation tube 110 (i.e., distance from distal end of the perforation tube 110 to distal end of the first grip portion 162) is preferably 100 mm to 300 mm.

FIG. 2C is a view schematically showing one example of the retractor 100 of the present invention, and is a schematic view of the retractor 100 showing a state in which a structure of the partial cocoon-shape is developed in the excluding section 122 of the developing body 120 extended from the perforation tube 110.

The retractor 100 of the present invention can develop the developing body 120 by further pushing and pulling at least one of the second grip portion 164 or the third grip portion 166 in the grip 160 with respect to the first grip portion 162. The developing body 120 includes the excluding section 122 and an introducing tube 130 extended from the excluding section 122, where the excluding section 122 is configured by a movable wire 124 and at least three fixing wires 126 arranged at the periphery of the movable wire 124. Moreover, the introducing tube 130 has a tubular shape, and the movable wire 124 is slidably passed therethrough. The number of fixing wires 126 arranged at the periphery of the movable wire 124 is not particularly limited, and is, for example three to nine, and preferably four to seven.

An example of a material configuring the introducing tube 130, the movable wire 124, and the fixing wire 126 independently includes stainless steel such as SUS304, resin such as polyamide, PTFE, and the like, stainless steel on which resin is coated, and the like. In particular, the movable wire 124 preferably has a line strength sufficient to withstand load at the time of exclusion, for example, line strength of greater than or equal to 1850 MPa, and preferably greater than or equal to 2100 MPa.

The movable wire 124 and the fixing wire 126 configuring the excluding section 122, as well as, the introducing tube 130 preferably have a smooth surface to prevent damage on the organ. Furthermore, a coating material having electrical insulating property may be applied on such surfaces to prevent generation of sparks with another surgical device during the surgery. The coating material may be a material normally used for coating of a medical instrument. For example, the coating material may be porous polytetrafluoroethylene (ePTFE) film, silicone film, polyurethane film, polyethylene terephthalate (Dacron®) film, and the like. The thickness of the coating layer formed by the coating material is not particularly limited, but is, for example, 4 μm to 16 μm, and preferably 8 μm to 12 μm.

The length of the excluding section 122 accommodated (undeveloped) in the perforation tube 110 fluctuates according to the size, and the like of the designed retractor, and hence is not necessarily limited. In one embodiment, the length of the excluding section accommodated in the perforation tube 110 is, for example, 40 mm to 120 mm, and preferably 50 mm to 80 mm. Moreover, in one embodiment, the size of the outer diameter of the excluding section 122 accommodated in the perforation tube 110 is, for example, 1.5 mm to 3 mm, and preferably 1.6 mm to 2 mm.

The length in the most developed state of the excluding section 122 and the maximum diameter of the partial cocoon shape formed when the fixing wire 126 of the excluding section 122 is developed (maximum diameter of when assumed that cut portion of the partial cocoon shape is compensated and complete cocoon shape is obtained), and the like fluctuate by the size of the designed retractor, and the like, and thus are not necessarily limited. In one embodiment, the length of the excluding section is, for example, 35 mm to 80 mm, and preferably, 45 mm to 65 mm. Furthermore, in one embodiment, the maximum diameter of the partial cocoon shape is, for example, 20 mm to 80 mm, and preferably, 35 mm to 60 mm.

Figure 3A:
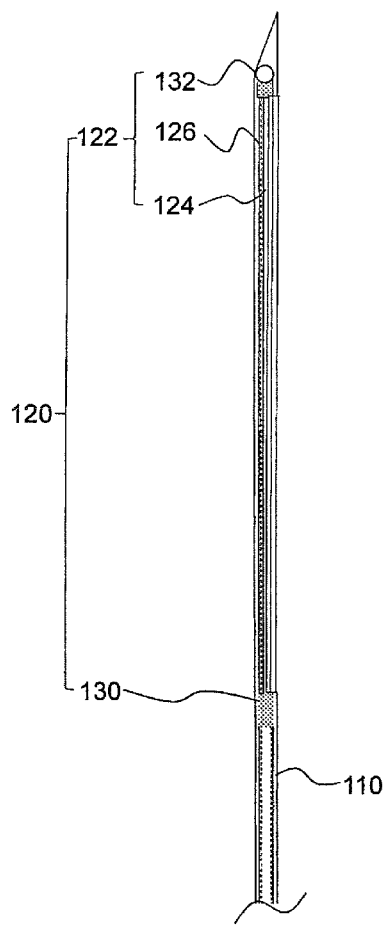
FIGS. 3A and 3B are views schematically showing one example of the developing body configuring the retractor of the present invention, where
Figure 3B:
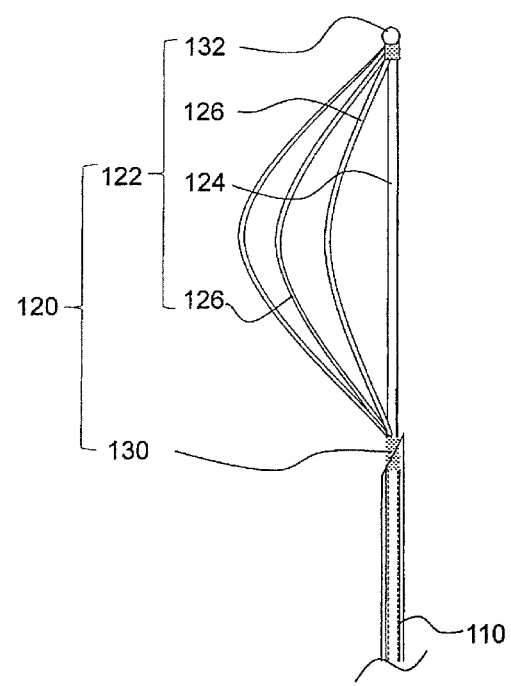

FIGS. 3A and 3B are views schematically showing one example of the developing body 120 configuring the retractor of the present invention.

As shown in FIG. 3A, the developing body 120 has the distal end of the movable wire 124 and the distal end of the fixing wire 126 joined at a cap 132 arranged at a tip of the distal end in the excluding section 122. The respective proximal ends of the fixing wires 126 are also fixed with the introducing tube 130, and the movable wire 124 is passed through the introducing tube 130. When the developing body 120 is accommodated in the perforation tube 110, for example, the distal end of the introducing tube 130 is located at the farthest position (i.e., more proximal side in the retractor 100) with respect to the ball shaped cap 132 made from SUS304, and the fixing wire 126 maintains a straightly extended state. Thus, the developing body 120 has a most deformed state in an axial direction of the perforation tube 110, and can freely slide in the perforation tube 110.

As shown in FIG. 3B, the developing body 120 can be extended from the perforation tube 110 so that the partial cocoon-shaped structure can be developed by the plurality of fixing wires 126. In such a state, each distal end of the movable wire 124 and the fixing wire 126 remains fixed to the cap 132, whereas the cap 132 and the distal end of the introducing tube 130 move closer and each fixing wire 126 causes deflection in a direction (radial direction) away from about the axis of the movable wire 124, and the partial cocoon-shaped structure by the entire plurality of fixing wires 126 can be built as the excluding section 122. The partial cocoon-shaped structure excludes the inside wall of the hollow organ or the organ in the body cavity, and can form a predetermined space in the hollow cavity or the body cavity.

Figure 4A:
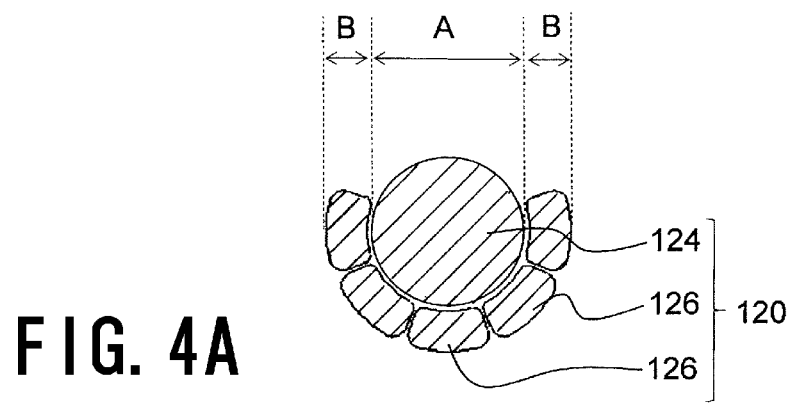
FIGS. 4A to 4D are views schematically showing examples of a cross-sectional view (cross-sectional view of movable wire and fixing wire) of the excluding section in a direction orthogonal to a long axis of the developing body configuring the retractor of the present invention, where
Figure 4B:
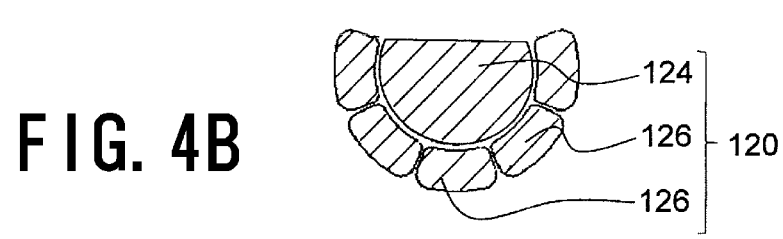
Figure 4C:
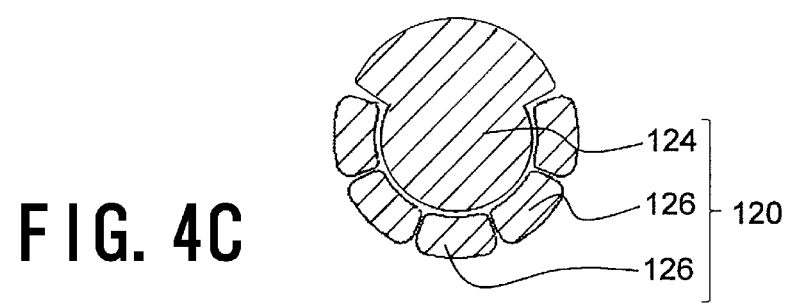

FIGS. 4A to 4D are views schematically showing examples of a cross-sectional view (cross-sectional view of movable wire 124 and fixing wire 126) of the excluding section 122 in a direction orthogonal to a long axis of the developing body 120 configuring the retractor 100 of the present invention. FIGS. 4A to 4C all show cross-sectional views of the excluding section when the excluding section 122 is not developed (i.e., in the accommodated state).

The movable wire 124 may have a substantially circular cross-section as shown in FIG. 4A, may have a cross-section including a shape in which an arc and a chord are combined (e.g., crescent shape) as shown in FIG. 4B, or may have a cross-section of a shape including a projection at one part of the chord in the shape in which the arc and the chord are combined as shown in FIG. 4C. Other cross-sectional shapes include shapes such as regular polygon (square, regular hexagon, regular octagon, etc.). Excluding one part, a plurality of fixing wires 126 having substantially the same cross-section shape are arranged at the periphery of the movable wire 124. A surface where each fixing wire 126 makes contact with the movable wire 124 preferably has a shape that coincides with the outer diameter of the movable wire 124. This is because the entire capacity of the excluding section 122 during the accommodation can be made as small as possible while avoiding an unnecessary space from being formed between the fixing wire 126 and the movable wire 124.

Figure 5A:
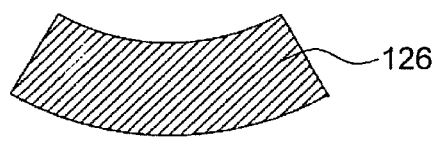
FIGS. 5A to 5C are cross-sectional views of the wire schematically showing an example of a cross-section of a fixing wire of the developing body configuring the present invention.
Figure 5B:
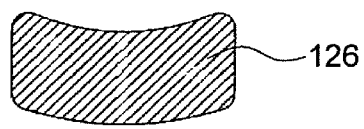
Figure 5C:
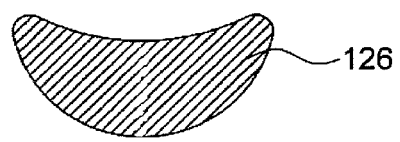

More specifically, the cross-section of the fixing wire 126 has a partial circular ring shape in which a part of the cross-section, as shown in FIGS. 5A to 5C, substantially coincides with a part of the outer periphery of the cross-section of the movable wire 124. In other words, the cross-section of the fixing wire 126 may have a shape as if a part of an arc is cut out as is from the circular ring as shown in FIG. 5A, may have a blunt shape in which four corners in the partial circular ring shape shown in FIG. 5A are rounded to reduce the damage of the surrounding tissues at the time of exclusion as shown in FIG. 5B, or may have a shape in which the respective cross-section is a crescent shape by having a portion corresponding to the outer edge side of the excluding section in the fixing wire 126 to a more rounded blunt shape as shown in FIG. 5C. The cross-section of the plurality of fixing wires 126 is preferably the same with respect to each other to carry out a uniform development.

Referring back to FIG. 4A again, the diameter A of the movable wire 124 and the thickness B of the fixing wire 126 are such that a ratio (A/B) of lengths preferably satisfies, for example two to ten, and preferably three to seven from the standpoint of easiness in the development of the fixing wire 126 and providing sufficient strength to each wire 124, 126. In one embodiment, A is 1.2 mm and B is 0.25 mm (A/B is 4.8).

Figure 4D:
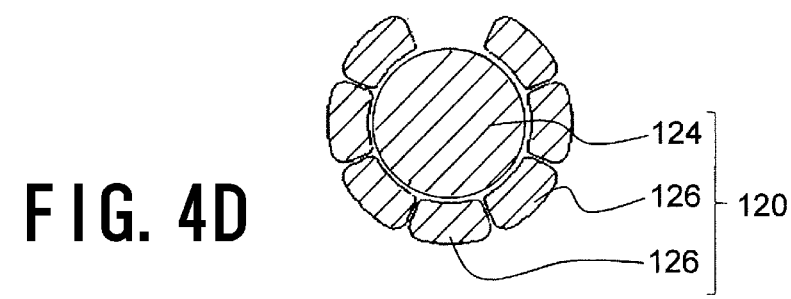
Figure 6:
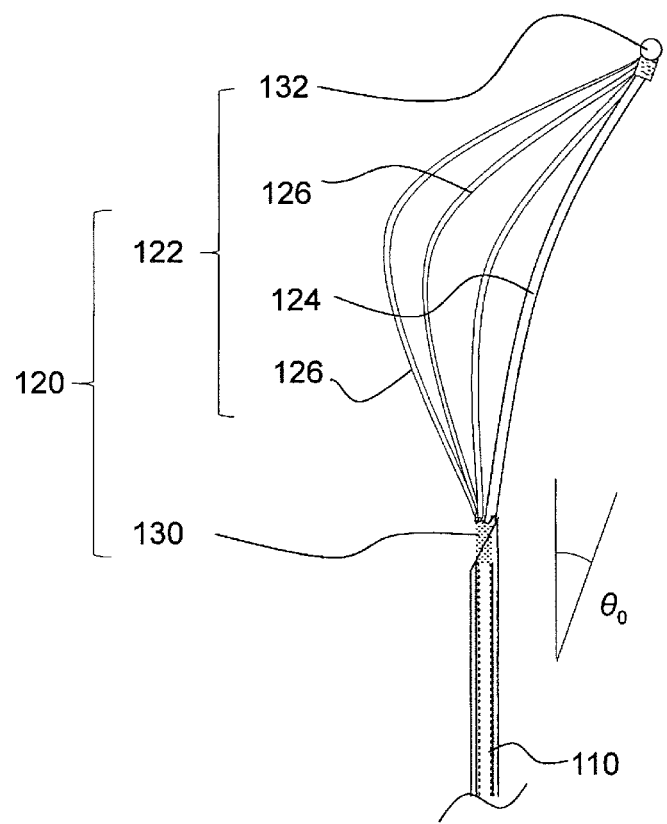
FIG. 6 is a view schematically showing another example of the developing body configuring the retractor of the present invention, and is a partially cutout cross-section view of a distal end portion of the retractor of the present invention showing a developing body extended from the perforation tube and developed to a cocoon shape.

In the retractor 100 of the present invention, the fixing wire 126 is arranged only at one part of the periphery of the movable wire 124, and the fixing wire is not arranged in the remaining periphery. Thus, according to the change in the diameter, the material, the cross-sectional shape, and the like of the movable wire 124, when the developing body 120 is opened, a bending force acts on a portion where the fixing wire 126 is not arranged in the periphery of the movable wire 124 so that the movable wire 124 can configure a self-deflected shape along an axial direction of the perforation tube 110 (more specifically, over the entire portion corresponding to the excluding section 122 in the movable wire 124) (FIG. 6). Furthermore, such deflection causes the excluding section 122 to curve with respect to the axial direction of the perforation tube 110 at the proximal side of the excluding section 122 (i.e., near distal end of introducing tube 130). The deflection of the movable wire 124 and the flexion of the excluding section 122 further enlarges the scale (substantial capacity) of the retraction, thus further enhancing the operability of the retractor. The retractor in which the excluding section 122 can flex with respect to the axial direction of the perforation tube 110 can be easily manufactured by, for example, selecting the cross-sectional shape of the movable wire and the arrangement of the fixing wire as shown in FIGS. 4A and 4D.

In the present invention, the flexion angle θ0 of the excluding section 122 is, for example 5° to 45°, and preferably 10° to 30°. The adjustment of the flexion angle θ0 of the excluding section 122 can be realized, for example, by selecting the movable wire 124 so as to have a lower strength than the fixing wire 126 or so as to have elasticity. A specific example includes:

(1) using twisted wire for the movable wire 124;

(2) processing the cross-section of the movable wire 124 to an irregular shape as shown in FIG. 4B, for example, (e.g., process direction desired for flexion of excluding section 122 on plain wire);

(3) setting the cross-sectional area of the movable wire 124 small with respect to the cross-sectional area of the fixing wire 126 (use thin wire for the movable wire 124); and (4) using material having low Young's modulus such as Ni—Ti alloy for the movable wire 124;

(5) using wire in which the movable wire 124 is deflected beforehand in the excluding section 122; and (6) combinations of a plurality of (1) to (5).

Alternatively, in order to avoid such flexion of the excluding section 122, for example, the deflection of the movable wire 124 to the portion where the fixing wire 126 is not arranged in the periphery of the movable wire 124 can be prevented or reduced by processing the wire configured to a shape having a projection at one part of the cross-section as shown in FIG. 4C.

Moreover, in the present invention, the number and arrangement of the fixing wires 126 with respect to the movable wire 124 are selected such that one developing angle θ2 is greater than the remaining developing angle θ1 and the developing angle θ2 has a predetermined angle among the developing angles formed between two adjacent fixing wires in the excluding section of when the developing body is developed.

The term "developing angle" used in the present specification refers to an angle formed between one fixing wire and a fixing wire adjacent thereto when the excluding section of when the developing body of the retractor is developed is seen from the distal end side of the retractor.

In the retractor of the present invention, such developing angle θ2 is 90° to 240°, preferably 120° to 240°, and more preferably 120° to 180°. The remaining developing angles (θ1) may be set to an angle substantially the same as each other or may be set to an angle different from each other as long as all the remaining developing angles θ1 are angles smaller than the developing angle θ2.

The relationship of the plurality of fixing wires 126 and the developing angles θ1 and θ2 will be described using specific examples.

Figure 7A:
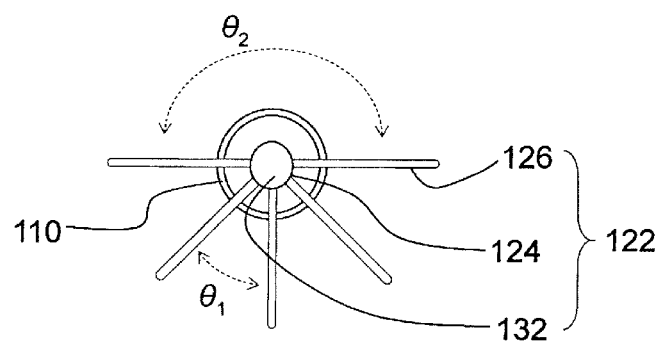
FIGS. 7A and 7B are views schematically showing an example of a tip of the distal end of the retractor when the developing body is extended from the perforation tube and developed in the retractor of the present invention, where
Figure 7B:
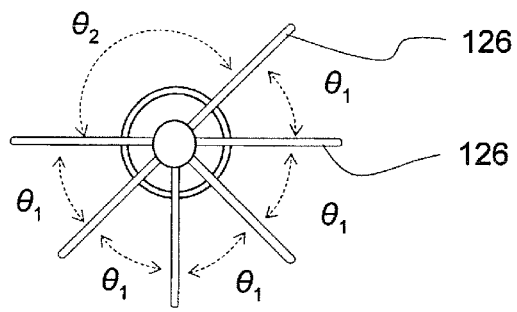

FIGS. 7A and 7B are views schematically showing an example of the tip of the distal end of the retractor when the developing body 120 is extended from the perforation tube 110 and developed in the retractor 100 of the present invention.

In the example shown in FIG. 7A, the fixing wire 124 of the excluding section 122 configuring the retractor of the present invention is configured by five fixing wires. Here, of the developing angles formed between two adjacent fixing wires, one developing angle θ2 is approximately 180° and the remaining developing angle θ1 is approximately 45°. In the example shown in FIG. 7B, the fixing wire 124 of the excluding section 122 configuring the retractor of the present invention is configured by six fixing wires. Here, of the developing angles formed between two adjacent fixing wires, one developing angle θ2 is approximately 135° and the remaining developing angle θ1 is approximately 45°.

In the present invention, the developing angle θ2 and another developing angle θ1 satisfy the above described relationship, so that a region of retraction where the operability is enhanced can be formed between the two fixing wires having the developing angle θ2 in the excluding section 122.

In the retractor of the present invention, the extension of the developing body from the accommodation tube, the accommodation of the developing body to the accommodation tube, and the development or the accommodation of the excluding section in the developing body are controlled by the grip provided at the proximal end side of the retractor.

Figures 8A, 8B, 8C:
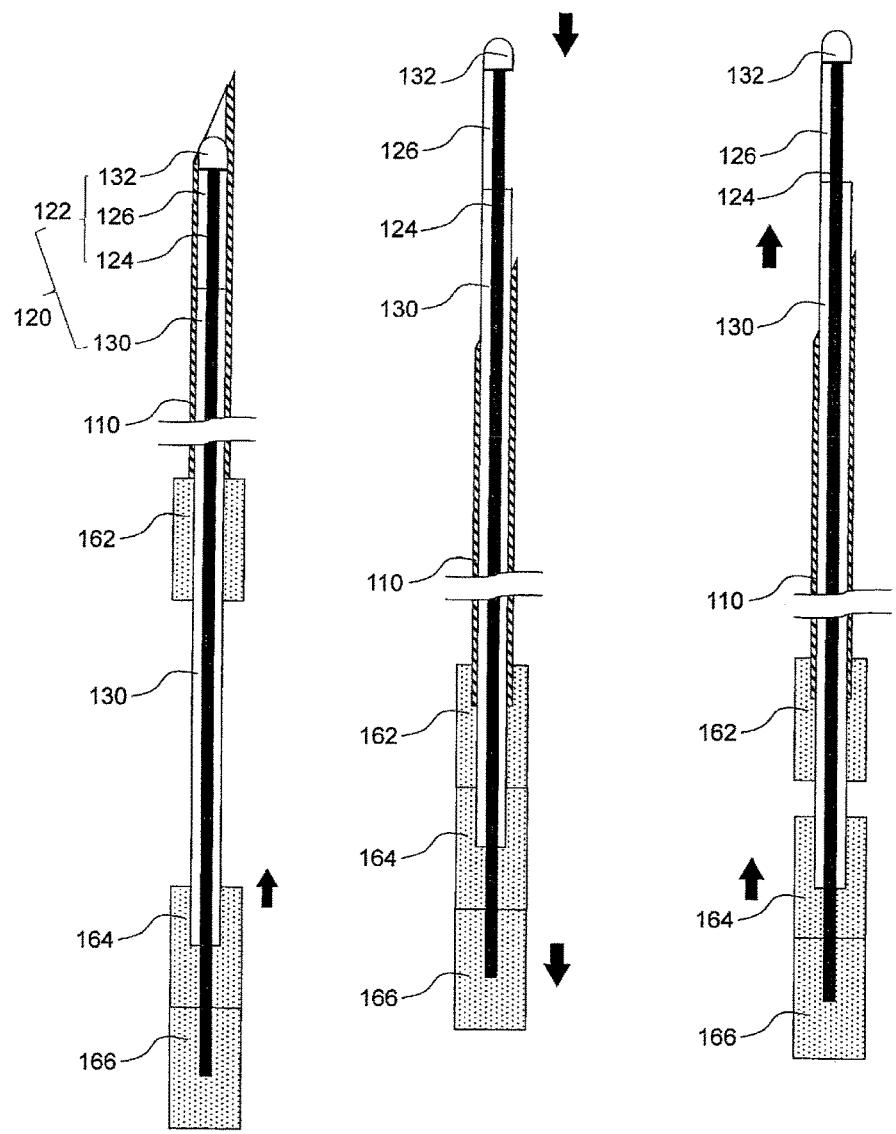
FIGS. 8A to 8C are schematic cross-sectional views of the retractor showing one example of the retractor of the present invention, where

FIGS. 8A to 8C are schematic cross-sectional views of the retractor showing one example of the retractor 100 of the present invention.

As shown in FIG. 8A, in the present invention, the proximal end of the perforation tube (accommodation tube) 110 is connected to the first grip portion 162, the proximal end of the introducing tube 130 of the excluding section 122 is connected to the second grip portion 164, and the proximal end of the movable wire 124 of the excluding section 122 is connected to the third grip portion 166. In the retractor 100 of the present invention, when the developing body 120 is accommodated in the perforation tube 110, the first grip portion 162, and the second grip portion 164 and the third grip portion 166 of the grip 160 are separated, as shown in FIG. 8A. In this state, the retractor 100 of the present invention is inserted to the inside wall of the hollow organ or the organ in the body cavity through an incision or by being directly perforated from the tip of the distal end of the perforation tube 110.

Next, the second grip portion 164 and the third grip portion 166 are respectively pushed in toward the distal end side, that is, the first grip portion 162 side with respect to the first grip portion 162. Thus, the introducing tube 130 and the movable wire 124 connected to the second grip portion 164 and the third grip portion 166, respectively, are pushed out toward the distal side, and the developing body 120 is extended from the perforation tube 110.

Thereafter, the development of the fixing wire 126 is carried out from the excluding section 122 in the developing body 120. The development of the fixing wire 126 from the excluding section 122 is carried out, for example, in the following manner according to the respective lengths of the introducing tube 130 and the movable wire 124 with respect to the length of the perforation tube 110, the position relationship of the second grip portion 164 and the third grip portion 166 with respect to the first grip portion 162 when the developing body 120 is extended from the perforation tube 110, and the like.

In other words, as shown in FIG. 8B, when the proximal end of the first grip portion 162 is brought into contact with or is substantially brought into contact with the distal end of the second grip portion 164 under a state the developing body 120 is extended from the perforation tube 110, only the movable wire 124 is sled toward the proximal side with the introducing tube 130 fixed with respect to the perforation tube 110 by pulling out only the third grip portion 166 toward the proximal side (hand side) with respect to the first grip portion 162 and the second grip portion 164. Thus, the distal end of the fixing wire 126 joined with the movable wire 124 at the portion of the cap 132 is also sled toward the proximal side. On the other hand, the proximal end of the fixing wire 126 is joined to the distal end of the introducing tube 130 and is in a fixed state, so that the fixing wire 126 is curved toward the outer side. As a result, the plurality of fixing wires 126 is developed in the excluding section 122, thus expressing the partial cocoon shape. The partial cocoon-shaped expression achieves exclusion of the inserted hollow organ or the body cavity.

Alternatively, as shown in FIG. 8C, when the first grip portion 162 and the second grip portion 164 are separated under a state the developing body 120 is extended from the perforation tube 110, only the introducing tube 130 is sled toward the distal side with respect to the perforation tube 110 and the movable wire 124 by pushing out only the second grip portion 164 toward the distal side with respect to the first grip portion 162 and the third grip portion 166. Thus, only the proximal end of the fixing wire 126 joined to the distal end of the introducing tube 130 is sled toward the distal side and the fixing wire 126 is curved toward the outer side while maintaining the position relationship of the movable wire 124 and the fixing wire 126 at the portion of the cap 132. As a result, the plurality of fixing wires 126 is developed in the excluding section 122, and a partial cocoon-shaped structure is expressed. The partial cocoon-shaped expression achieves the exclusion of the inserted hollow organ or the body cavity.

In FIGS. 8B and 8C, the length of pulling out or pushing out the third grip portion 166 and/or second grip portion 164 is fluctuated, so that the size of the partial cocoon-shaped structure expressed in the excluding section 122 can be freely changed.

The retractor of the present invention is not necessarily limited to the trocar or the pallium tube including the perforation tube as described above.

Figure 9:
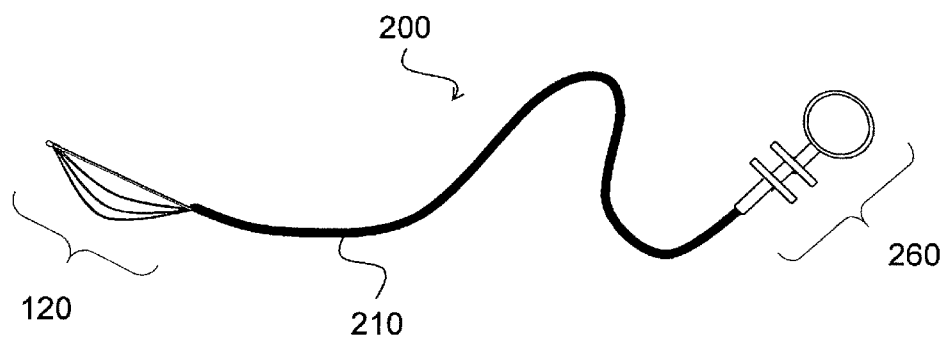
FIG. 9 is a view showing another example of the retractor of the present invention, and is a schematic view of the retractor including a developing body at a distal end of a longitudinal tube having flexibility.

FIG. 9 is a schematic view showing another example of the retractor of the present invention.

In FIG. 9, a retractor 200 of the present invention includes a developing body 120, a longitudinal tube 210 having flexibility, which serves as another example of an accommodation tube in which the developing body 120 can be accommodated and extended, and a grip 260 connected to respective proximal ends of the longitudinal tube 210 and the developing body 120.

The retractor 200 shown in FIG. 9 functions as a so-called snake retractor by providing flexibility to the longitudinal tube 210, and for example, can be freely passed through the hollow cavity. Other than using the longitudinal tube 210 instead of the perforation tube, the specific configurations of the developing body 120 and the grip 260 are similar to those in the retractor 100 of the present invention.

The retractor of the present invention is used to carry out exclusion in various surgeries in the hollow organs such as stomach, small intestine, large intestine, and vagina as well as the other organs such as liver, pancreas, kidney, gallbladder, spleen, uterus, lungs, and the like.

For example, in the surgery of stomach and esophagus, the retractor of the present invention is inserted to the lower surface of the hepatic left lobe interfering with the operative field to elevate it toward the abdominal side, so that the surgery can be proceeded more safely and efficiently without the interference to the operative field. Similarly, in the operation at the pelvic floor, the surgical operation of the periphery of the rectum can be efficiently carried out by spreading the uterus using the retractor of the present invention.

INDUSTRIAL APPLICABILITY

According to the present invention, a retractor that can freely exclude the organ can be provided. Furthermore, according to the present invention, the retractor is also useful in that gas-less surgery can be carried out, for example, as the field of view and the operation space can be ensured without injecting gas into the body cavity.

REFERENCE SIGNS LIST 100, 200 retractor
110 perforation tube
120 developing body
122 excluding section
124 movable wire
126 fixing wire
130 introducing tube
132 cap
160, 260 grip
162 first grip portion
164 second grip portion
166 third grip portion
210 longitudinal tube with flexibility

The invention claimed is:

1. A retractor for excluding an inside wall of a hollow organ or an organ in a body cavity, the retractor comprising:
   an accommodation tube;
   a developing body that is configured to be accommodated and extended with respect to the accommodation tube; and
   a grip connected to respective proximal ends of the accommodation tube and the developing body, wherein the developing body includes
      an excluding section configured by a movable wire and at least three fixing wires arranged at a periphery of the movable wire, and
      an introducing tube extended from the excluding section, the movable wire being passed through the introducing tube;
   a distal end of the movable wire and a distal end of the fixing wire are joined in the excluding section;
   among developing angles formed between two adjacent fixing wires in the excluding section when the developing body is developed, one developing angle $\theta 2$ is greater than a remaining developing angle $\theta 1$; and
   the developing angle $\theta 2$ is 90° to 240°.

2. The retractor according to claim 1, wherein the accommodation tube is a rigid perforation tube.

3. The retractor according to claim 2, wherein the excluding section is flexed with respect to an axial direction of the perforation tube when the developing body is developed.

4. The retractor according to claim 1, wherein
   the grip includes a first grip portion, a second grip portion, and a third grip portion from a distal side;
   a proximal end of the accommodation tube is connected to the first grip portion;
   a proximal end of the introducing tube of the excluding section is connected to the second grip portion; and
   a proximal end of the movable wire of the excluding section is connected to the third grip portion.

5. The retractor according to claim 1, wherein a cross-section of the movable wire has a substantially circular shape.

6. The retractor according to claim 1, wherein a curve of the fixing wire in the excluding section is controlled by pushing or pulling at least one of the second grip portion or the third grip portion with respect to the first grip portion.

7. The retractor according to claim 1, wherein the accommodation tube is a longitudinal tube having flexibility.

* * * * *